(12) United States Patent
Richardson et al.

(10) Patent No.: US 8,773,269 B2
(45) Date of Patent: Jul. 8, 2014

(54) AUTONOMOUS FALL MONITOR

(76) Inventors: Neal T. Richardson, Charlottesville, VA (US); B. Eugene Parker, Jr., Charlottesville, VA (US)

( * ) Notice: Subject to any disclaimer, the term of this patent is extended or adjusted under 35 U.S.C. 154(b) by 521 days.

(21) Appl. No.: 12/492,924

(22) Filed: Jun. 26, 2009

(65) Prior Publication Data
US 2009/0322540 A1    Dec. 31, 2009

Related U.S. Application Data

(60) Provisional application No. 61/129,465, filed on Jun. 27, 2008, provisional application No. 61/213,149, filed on May 12, 2009.

(51) Int. Cl.
*G08B 23/00*    (2006.01)

(52) U.S. Cl.
USPC .............. 340/573.7; 340/573.1; 340/539.11

(58) Field of Classification Search
CPC ............................ A61B 5/1117; A61B 5/1116
USPC ................ 340/573.7, 573.1, 539.11, 539.12; 600/300
See application file for complete search history.

(56) References Cited

U.S. PATENT DOCUMENTS

| | | | | |
|---|---|---|---|---|
| 6,433,690 B2* | 8/2002 | Petelenz et al. | ............ | 340/573.1 |
| 7,328,612 B2* | 2/2008 | Jamsen et al. | ............ | 73/379.01 |
| 7,548,168 B2* | 6/2009 | Ishikawa et al. | ............ | 340/573.1 |
| 7,733,224 B2* | 6/2010 | Tran | .............................. | 340/540 |
| 7,893,844 B2* | 2/2011 | Gottlieb | ...................... | 340/573.1 |
| 2005/0067816 A1* | 3/2005 | Buckman | ................... | 280/730.1 |
| 2006/0270949 A1* | 11/2006 | Mathie et al. | ................. | 600/595 |
| 2007/0027704 A1* | 2/2007 | Patel et al. | ........................ | 705/1 |
| 2008/0129518 A1* | 6/2008 | Carlton-Foss | ............. | 340/573.1 |

OTHER PUBLICATIONS

"Acceleration Insensitive Semiconductor Pressure Sensors for High Bandwidth Measurements on Rotating Turbine Blades" A.D. Kurtz, et al; 8 pages.
"Barometric Pressure and Triaxial Accelerometry-Based Falls Event Detection" Federico Bianchi, et al. IEEE Transactions on Neural Systems and Rehabilitation Engineering, vol. 18, No. 6 Dec. 2010; pp. 619-627.
"A New Device to Estimate VO2 during incline Walking by Accelerometry and Barometry" Toshiaki Yamakazi, et al. Department of Sports Medical Sciences, Shinshu University Graduate School of Medicine, Matsumoto, Japan; Jukunen Tai-iku Daigaku Research Center, Matsumoto, Japan; and Kissei Comtec, Co., Ltd., Matsumoto Japan; pp. 2213 to 2219.
"Classification of Human Moving Patterns Using Air Pressure and Acceleration" Koichi Sagawa, et al. GSIS, Tohuku University, Toshiba CO, Ltd.; pp. 1214 to 1219.

(Continued)

*Primary Examiner* — Steven Lim
*Assistant Examiner* — Hongmin Fan
(74) *Attorney, Agent, or Firm* — Baker & Hostetler LLP

(57) ABSTRACT

A system, a method and an apparatus for autonomous monitoring, detecting and tracking of movement and orientation of a body or portion of a body. The apparatus comprises a device configured to monitor the translational and/or rotational movement of the body; and an altimeter configured to measure changes in height of the body. An alert condition is determined based on the translational and/or rotational movement of the body and changes in height of the body or portion of the body. The alert condition may comprise a hard fall event, a soft fall event, a susceptibility to a fall, or a near fall event.

20 Claims, 8 Drawing Sheets

(56) References Cited

OTHER PUBLICATIONS

"Improvement of Walking Speed Prediction by accelerometry and Altimetry, Validated by Satellite Positioning" O. Perrin, et al. Medical & Biological Engineering & Computing 2000, vol. 38 164-168.
"Automatic Classification of Ambulatory Movements and Evaluation of Energy Consumption Utilizing Accelerometers and Barometer" Yasuaki Ohtaki, et al. Jul. 22, 2003 / Accepted: Nov. 6, 2003 / Published online: Aug. 10, 2005 © Springer-Verlag 2005; pp. 1034 to 1040.
Verification and Validation of Neural Networks for Safety-Critical Applications; Jason Hull & David Ward Barron Associates, Inc.; Radoslaw R. Zakrzewski Goodrich Aerospace, Fuel and Utility Systems.
Run-Time Validation and Verification for Safety-Critical Flight Control Systems; Prepared by Barron Associates: Carl R. Elks et al; Feb. 11, 2005, pp. 1-95.
J Am Geriatr Soc. Jul. 1988;36(7):613-6; Forgetting Falls. The limited accuracy of recal of falls in the elderly; Cummings SR et al; Division of General Internal Medicine, University of California, San Francisco 94143.
The Pattern of Muscular Activity During the Arm Swing of Natural Walking; Maria L. Fernandez Ballesteros2 et al; 2Institute of Neurophysiology; University of Copenhagen, and the Laboratory of Clinical Neurophysiology, University Hospital, Copenhagen, Denmark 1Working under a W.H.O. fellowship.
Fall Risk Factors in Parkinson's Disease; Peggy Gray et al; Journal of Neuroscience Nursing, Aug. 2000 vol. 32, No. 4; pp. 222-228.
USA Today, Apr. 6, 2004; 6D "A nation of caregivers' Study counts an increasing number of Americans providing for an adult—and the boomer bubble hasn't even burst yet" Jane Kornblum; pp. 1-4.
BMC Women's Health; Report; Multiple Roles and Women's Mental Health in Canada; Heather Maclean*1 et al; BioMed Central; Published Aug. 25, 2004; BMC Women's Health 2004, 4(Suppl 1):S3 doi:10.1186/1472-6874-4-SI; pp. 1-9.
Caring for Frail Elderly Parents: A Comparison of Adult Sons and Daughters1; Ada C. Mui, Phd; Columbia University School of Social Work, 622 W. 113th Street, New York, NY 10025; Received Jun. 18, 1993; Accepted Oct. 4, 1994.
Modification of Postural Responses and Step Initiation: Evidence for Goal-Directed Postural Interactions; Journal of Neurophysiology; vol. 72, No. 6, Dec. 1994; Printed in the USA; A.L. Burleigh et al; R.S. Dow Neurologicial Sciences Institute, Portland, Oregon 97209; pp. 2892-2902.
Postural feedback responses scale with biomechanical constraints in human standing; Research Article; Sukyung Park et al; Dec. 30, 2002, © Springer-Verlag 2003.
Phase-Dependent modulation of proximal and distal postural response to slips in young. and older adults; Pei-Fan Tang et a; J Gerontal A Biol Sci Med Sci. Feb. 1999; 54(2) :M89-102; Department of Exercise and Movement Science and Institute of Neuroscience, University of Oregon, Eugene USA, pftang@hc.mc.ntu.edu.tw.
Inefficient Postural Responses to Unexpected Slips During Walking in Older Adults; Pei-Fan Tang et al; Motor Control Laboratory, Department of Exercise and Movement Science and Institute of Neuroscience, University of Oregon; Journal of Gerontology: Medical Sciences 1998, vol. 53A, No. 6. M471-M480 © 1998 by the Gerontological Society of America.
Preventing Falls in Elderly Persons; Mary E. Tinetti, M.D.; The New England Journal of Medicine; Downloaded from www.nejm.org at University of Virginia on Apr. 18, 2010 © 2003 Massachusettes Medical Society; pp. 42-49.
Age-Related Differences in Laterally Directed Compensatory Stepping Behavior; Brian E. Maki et al; Journal of Gerontology: Medical Sciences 2000, vol. 55A, No. 5, M270-M277 © 2000 by the Gerontological Society of America.
Sensitive low-cost altimeter for schools; Physics Education; T. Lewowski Institute of Experimental Physics, Sep. 2005; pp. 416.
Screening for Osteoporosis in Men: A Systematic Review for an American College of Physicians Guideline; Hau Liu, MD, MBA, MPH et al; Annals of Internal Medicine Clinical Guidelines; May 6, 2008, vol. 148, No. 9; pp. 685-702.
Screening for Osteoporosis in Men: A Clinical Practice Guideline from the American College of Physicians; Amir Qaseem, MD, PhD, et al; MS, for the Clinical Efficacy Assessment Subcommittee of the American College of Physicians; © 2008 American College of Physicians, May 6, 2008, pp. 680-685.
Statistical power calculations; R. V. Lenth; J. Anim. Science; 2007; 85(E. Suppl.); E24-E29.
False Alarm Estimation in an Automated Fingerprint Identification System (AFIS); R. Khanna et al; IEEE; © 2000, pp. 260-261.
Neuronal coordination of arm and leg movements during human locomotion; V. Dietz et al; European Journal of Neuroscience; vol. 14; 2001; pp. 1906-1914.
Effect of slip on movement of body center of mass relative to base of support; Jia-Yuan You et al; Clinical Biomechanics; vol. 16, (2001); pp. 167-173.
Role of the Unperturbed Limb and Arms in the Reactive Recovery Response to an Unexpected Slip During Locomotion; D. S. Marigold et al; J Neurophysiological; vol. 89, 2003, pp. 1727-1737.
Strategies for Dynamic Stability During Locomotion on a Slippery Surface: Effects of Prior Experience and Knowledge; J. Neurophysiological; vol. 88, 2002, pp. 339-353.
The Role of Limb Movements in Maintaining Upright Stance: The "Change-in-Support" Strategy; B. E. Maki et al; Physical Therapy; vol. 77; No. 5; May 1997; pp. 488-507.
Early activation of arm muscles follows external perturbation of upright stance; W. E. McIlroy et al; Neuroscience Letters; vol. 184, (1995), pp. 177-180.
Control of rapid limb movements for balance recovery: age-related changes and implications for fall prevention; W. E. McIlroy et al; Age and Ageing; 2006; 35-S2; pp. ii 12-ii 18.
Fall arrest strategy affects peak hand impact force in a forward fall; K. M. DeGoede et al; Journal of Biomechanics; vol. 35, (2002), pp. 843-848.
Effect to the "squat protective response" on impact velocity during backward falls; S. N. Robinovitch et al; Journal of Biomechanics; vol. 37, (2004), pp. 1329-1337.
Postural steadiness during quiet stance does not associate with ability to recover balance in older women; D. C. Mackey et al; Clinical Biomechanics; vol. 20, (2005), pp. 776-783.
Postural abnormalities to multidirectional stance perturbations in Parkinson's disease; M. G. Carpenter et al; J. Neural Neurosurgery Psychiatry; 2004; vol. 75, pp. 1245-1254.
Age-dependent variations in the directional sensitivity of balance corrections and compensatory arm movements in man; J.H.J. Allum et al; Journal of Physiology (2002); 542.2; pp. 643-663.
Hip Impact Velocities and Body Configurations for Voluntary Falls From Standing Height; A.J. van den Kroonenberg; et al; J. Biomechanics. vol. 29, No. 6, 1996, pp. 807-811.
Common protective movements govern unexpected falls from standing height; E. T. Hsiao et al; Journal of Biomechanics; vol. 31, (1998), pp. 1-9.
Telecare Home Monitor; B. Eugene Parker, Jr., Ph.D.; Barron Associates, Inc.; pp. 1-13.
PHS/NIAMS Muscle Biology, Exercise Physiology, and Sports Medicine, Topic A: Muscle Biology Branch, Subtopic 2; Eugene Parker, Jr., Ph.D.; Barron Associates, Inc.; J282; pp. 1-18.
A Low-Cost Fall Monitor for Geriatric Subjects; M. J. Geary et al; Barron Associates, Inc; University of Kansas, Human Motion Control Lab Department of Mechanical Engineering; Nov. 2006; J289; pp. 1-13.
Speedy: A Fall Detector in a Wrist Watch; T. Degen et al; Swiss Federal Institute of Technology Electronics Laboratory and Swiss Federal Institute of Technology Department of Information Technology and Electrical Engineering; pp. 1-4.
Early activation of arm and leg muscles following pulls to the waist during walking; J. E. Misiaszek; Exp Brain Res; (2003) vol. 151, pp. 318-329.
Statistical Methods for Assessing Agreement Between Two Methods of Clinical Measurement; J. M. Bland et al; Department of Clinical Epidemiology and Social Medicine; pp. 1-9.

* cited by examiner

AUTONOMOUS FALL MONITOR

CROSS REFERENCE TO PRIOR APPLICATIONS

This application claims priority and the benefit thereof from a U.S. Provisional Application No. 61/129,465, filed on Jun. 27, 2008, and U.S. Provisional Application No. 61/213,149 filed May 12, 2009, both of which are hereby incorporated by reference for all purposes as if fully set forth herein.

FIELD OF THE INVENTION

The invention relates to an apparatus, a method and a system for monitoring, detecting and tracking body orientation and/or motion, including a fall or near fall event condition.

BACKGROUND OF THE INVENTION

Body orientation/motion monitoring and particularly fall monitoring is very useful to a wide range of subjects, from elderly persons to emergency workers to race horses to anthropomorphic robots. While the ability to detect a hard impact fall is important in all cases, additional information about "soft" falls, such as, for example, when a person is overcome by smoke and slowly sinks to the ground, or near-falls, as in when a race horse stumbles, are also important events to detect. Prior fall detection and monitoring technology has taken many forms. Some previous inventions have employed accelerometers in a waist-worn device to detect human falls. Although wrist-worn devices with accelerometers are relatively successful at detecting some "hard" falls, which are defined as sudden and rapid descents that are usually associated with a high-g impact, these devices have numerous drawbacks, including, for example, difficulty detecting backward and lateral falls and an inability to sense the difference between a person lying down and a person who has fallen. Thus, these prior systems cannot be used when a person is at rest or when a person experiences a "soft" fall without an impact (e.g., a firefighter that is slowly overcome by smoke and slowly sinks to the ground). Furthermore, these systems may completely miss near-fall events, such as, for example, when an elderly person trips and grabs onto a railing in order to avoid a fall or a stumble or gait change event that might precede a hard fall. In fact, prior work, such as, e.g., the commercially available system described at <<http://www-.dynamic-living.com/pers-info.htm#fall>> can include disclaimers like "The Fall Detector cannot differentiate between a fall and simply lying down to rest. You will need to remove it before you lie down and then put it back on when you get up."

An example of a device presently available commercially that can monitor body orientation and movement patterns in free-living subjects is the Intelligent Device for Energy Expenditure and Physical Activity (IDEEA) (Minisun, Fresno, Calif.), as described in Zhang K, Werner P, Sun M, Pi-Sunyer F X, Boozer C N, "Measurement of human daily physical activity," Obes Res, Jan. 11, 2003(1):33-40. This accelerometer-based device is costly and requires the use of five sensors that are taped directly to the skin (e.g., chest, both thighs, and bottom of both feet) and associated cable tethers to attach the sensors to a waist-worn data-recording unit. The manufacturer claims that the IDEEA can identify various body postures and types of physical activity, including lying, sitting, walking, climbing stairs, running, and jumping.

Another example is the BodyTrac system (IMSystems, Baltimore, Md.), which includes a body posture and movement pattern recorder nominally worn as a chest band. The BodyTrack system employs a 5.8 cm×3.4 cm×1.7 cm module containing a sealed sphere with a bolus of mercury that, depending on body posture, short different sets of contacts. The BodyTrac system is claimed to provide the following body posture information: upright, walking, lying supine, lying right, lying left, and lying prone. A major limitation of the BodyTrac system appears to be an inability to discriminate between sitting and standing; to accomplish this, the BodyTrac system employs a second monitor that must be worn on a thigh, as described by Gorny S W, Allen R P, Krausman D T, Cammarata J., "Initial demonstration of the accuracy and utility of an ambulatory, three-dimensional body position monitor with normals, sleepwalkers and restless legs patients," Sleep Med, March 2001; 2(2):135-143.

Other currently available devices used to monitor falls, such as, e.g., described in Pervasive Computing, "A Smart Sensor to Detect the Falls of the Elderly," Sixsmith, Andrew; Johnson, Neil Vol. 3, No 2 pp 42-47, include sophisticated visual monitoring systems and "smart homes" that feature sensors embedded in floors or infrared beams positioned near the floor. Although some of these systems may provide autonomous notification aspects, none allow for the detection of near falls, and none would allow for the detection of falls outside of the subject's home. Therefore, these devices would not prove useful for emergency workers, individuals with seizures, race horses, or the like.

Thus, a long felt, unfulfilled need exists for an apparatus, system and method that may monitor and detect a fall event type by a user, such as, for example, but not limited to, an emergency worker, an individual with a medical condition, a race horse, or the like.

SUMMARY OF THE INVENTION

According to principles of the invention, a system, an apparatus, and a method are provided for autonomous monitoring, detecting and tracking of body, motion and orientation including fall and near-fall events. The apparatus comprises a communicator for autonomous monitoring, detecting and tracking of movement and orientation of a body or portion of a body, comprising: a device configured to monitor the translational and rotational movement of the body; and an altimeter configured to measure changes in height of the body, wherein an alert condition is determined based on the translational and rotational movement of the body and changes in height of the body or portion of the body. The alert condition may comprise: a hard fall event; a soft fall event; a susceptibility to a fall; or a near fall event. The device configured to monitor the translational and rotational movement of the body, or portion of a body, may comprise one or more triaxial accelerometers and wherein the one or more altimeters may comprise a high sensitivity pressure sensor. The device may further comprise one or more gyroscopes.

The communicator may further comprise: a sensor configured to monitor biological functions of the body; and/or a storage configured to collect and store data for synchronous communication to a transceiver, wherein the data comprises any one or more of a date data, a time data, a location data, a biometric data and an alert condition data.

The communicator may further comprise one or more actuators configured to be actuated by a user to enable or disable an alert call, wherein the one or more actuators are configured to attach to the body.

The communicator may further comprise a transceiver unit configured to convey the data stored in the storage to a transceiver, wherein the transceiver is configured to provide notification of alert events to one or more recipients.

In the communicator, monitored translational and rotational movement of the body may include standing, walking, running, sitting, falling and lying down. The transceiver unit may be further configured to synchronize data with another communicator prior to monitoring translational and rotational movement of the body and measuring changes in height of the body or portion of the body.

A system is provided that includes the communicator, wherein the system further includes the transceiver. The transceiver may comprise a communications device configured to record, log and track the data conveyed from the transceiver unit. The transceiver may further comprise a storage that stores the recipient information.

According to a further aspect of the invention, a transceiver is provided for autonomous monitoring, detecting and tracking of orientation, translational or rotational movement of a body, comprising: a transceiver unit configured to receive alert status data from a communicator; and a storage configured to hold recipient information associated with the communicator, wherein the transceiver unit is further configured to notify one or more recipients on the basis of the alert status data. The transceiver unit may be further configured to provide notification of an alert event to the recipient. The transceiver may further comprise a communication device that is configured to record, log and track the alert status data.

According to a still further aspect of the invention, a method is provided for autonomously monitoring, detecting and tracking movements of a body, comprising: monitoring a translational and a rotational movement of the body or portion of it; measuring a change in height of the body or a portion of the body; and determining an alert event based on the translational and rotational movement of the body and the change in height of the body or portion of it.

The method may further comprise: generating an alert status data based on the determined alert event; and contacting one or more recipients based on the fall status data.

The method may further comprise: selecting a recipient from the contact list; retrieving a message to be conveyed to the recipient; and conveying the message to the recipient.

The method may further comprise determining whether the recipient responds to the message. The fall status data may comprise: translational movement data; rotational movement data; height data; height change data; time data; date data; location data; or biometrics data.

The method may further comprise activating a communication device to establish a communication session with the recipient, when the recipient responds to the message.

Additional features, advantages, and embodiments of the invention may be set forth or apparent from consideration of the following detailed description and drawings. Moreover, it is noted that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced.

Figure 1:
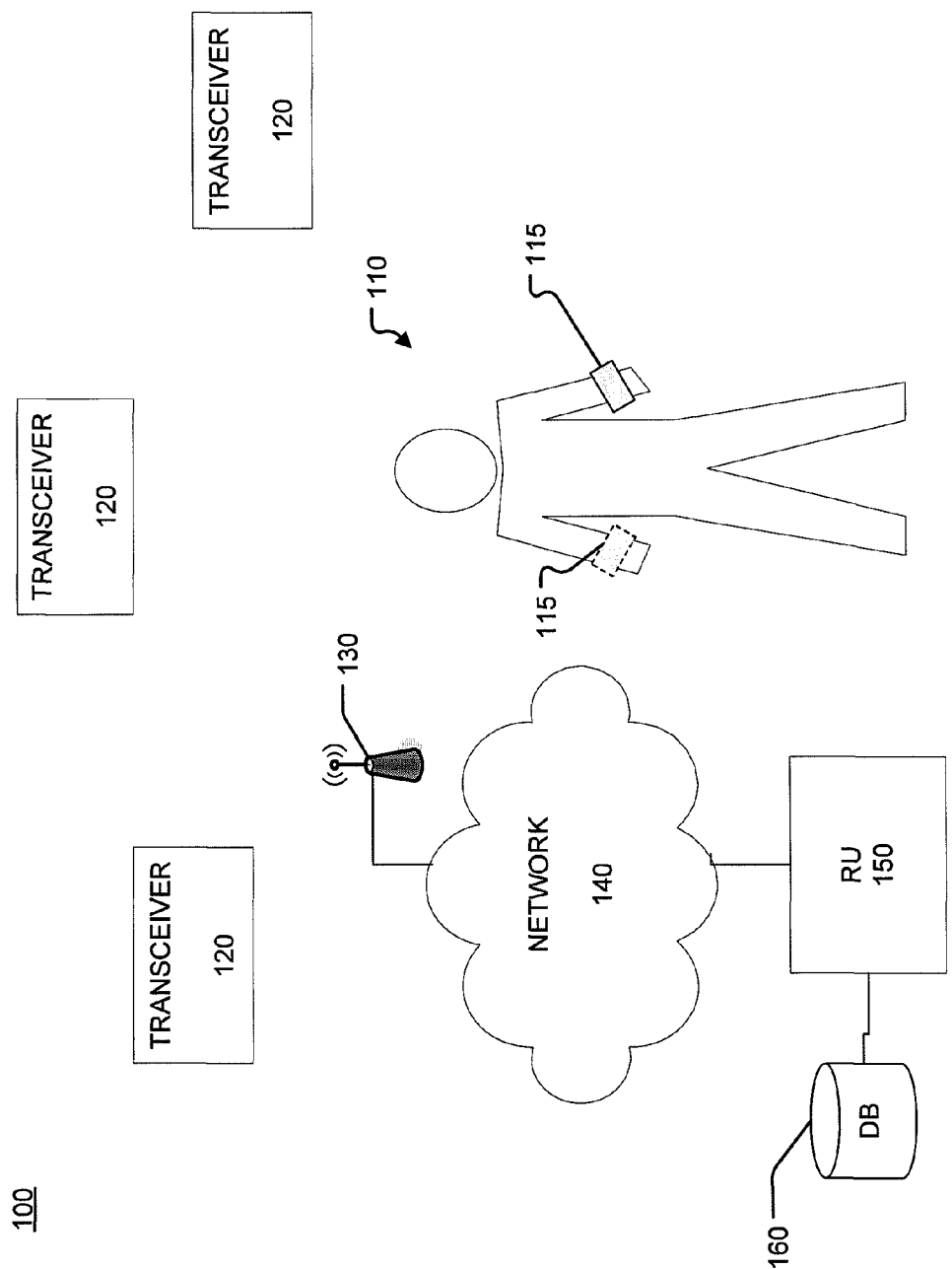
FIG. 1 shows an example of a fall monitoring (FM) system, according to principles of the invention.

The present invention is further described in the detailed description that follows.

DETAILED DESCRIPTION OF THE INVENTION

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings.

FIG. 1 shows an example of a fall monitoring (FM) system 100, according to principles of the invention. The FM system 100 comprises a fall monitoring (FM) communicator 115 and one or more transceivers 120. The FM system 100 may further comprise an access point 130, a network 140, a response unit (RU) 150a database(s) 160, and/or one or more additional FM communicators 115 (not shown).

The FM communicator 115 may include, for example, but is not limited to, a portable computer such as, e.g., an electronic device configured to accept data, perform prescribed mathematical and logical operations at high speed, and output the results of these operations. The FM communicator 115 may be configured to communicate with the one or more transceivers 120, the access point 130 and/or another FM communicator 115 (shown in cross-hatched lines). For example, the FM communicator 115 may include the pressure sensor described in "Sensitive low-cost altimeter for schools," by Lewowski T., *Physics Ed*, September 2005; 40(5):416.

The FM communicator 115 may be configured to be attached to a portion of, for example, but not limited to, a body (e.g., a wrist, a leg, or the like) of the user 110. The FM communicator 115 may detect and determine an orientation (or position) and/or movement patterns of the user 110. The FM communicator 115 may provide discrimination of position, particularly as it relates to, for example, height measurements, like standing, lying or sitting orientations of the user 110, as well as any changes to those positions, such as, for example, falling, jumping, or the like. In this regard, the FM communicator 115 may be configured to sense pressure changes relatively rapidly to eliminate potential confounding caused by changes in, for example, barometer pressure (e.g., due to weather, geographic location, or the like). For example, if mounted on an ankle, the FM communicator 115 may discriminate a walking condition from a standing condition of the user 110, as well as a standing condition from a lying in a bed condition. The FM communicator 115 may provide further information concerning various other body orientations (e.g., lying prone, supine, on one's side, or the like) and movement patterns.

It is noted that the FM communicator 115, including accelerometer(s) and pressure sensor(s), may reside in a single module (shown in FIG. 1) or multiple modules (not shown). According to the preferred embodiment, the FM communicator 115 resides in a single module configuration. In a multiple module configuration, the accelerometer(s) and pressure sensor(s) may be provided as separate modules, each of which may be mounted to a different portion of the body of user 110. Additionally, multiple sensor packages may be mounted on the body of the user 110 for further information gathering, which can store data within the package and/or wirelessly transmit the data to the transceiver 120, the access point 130, the RU 150 and/or another FM communicator 115.

The FM communicator 115 may further comprise a body orientation monitor (not shown), which may track, for example, body posture and movement of the user 110. For example, the FM communicator 115 may include a torso-mounted, triaxial accelerometer-based actigraph with built in electrodes for heart-rate monitoring in addition to a high-sensitivity pressure sensor. The FM communicator 115 may further comprise one or more gyroscopes. The tracked data may be processed and used to better understand daily activity patterns and body orientations for health care and/or research applications, as well for monitoring the well-being of the user 110.

The transceiver 120 may include a computer (e.g., an electronic device configured to accept data, perform prescribed mathematical and logical operations at high speed, and output the results of these operations), such as, for example, but not limited to, a personal computer, a laptop computer, a palmtop computer, a notebook computer, a desktop computer, a workstation, a server, a multimedia player, smartphone or any combination of the foregoing, or the like. The transceivers 120 may be configured to synchronously (or asynchronously) receive fall status data, including sensor data, from the FM communicator 115. The transceiver 120 may be further configured to record, log, and track the fall status data, and may provide notification of fall events to the RU 150. The RU 150 may include, for example, but is not limited to, emergency personnel, family members, caregivers, friends, or any other entity that may desire to monitor, track or detect a fall status condition of the user 110. In this regard, the transceiver 120 may transmit fall event data to the RU 150, which may be relied upon for, for example, fall and near-fall detection. In this regard the data may be conveyed directly (e.g., over the network 140) from the transceiver 120 to the RU 150, or through the access point 130.

The transceiver 120, which may be either portable or stationary, may include a telephone console (not shown). The telephone console, which may include a built-in speakerphone, may be configured to deliver a pre-recorded message to a prioritized list of caregivers, to ensure that the fall event notification is received by a human being, rather an answering machine. The telephone console may be further configured to receive a wearer-initiated personal emergency alert call and/or alert call cancel request from the FM communicator 115. The telephone console may comprise a mobile telephone device, such as, e.g., but not limited to, a cellular telephone, a wired telephone, a two-way communication device, a software defined radio (SDR), or the like.

The RU 150 may also include a computer (e.g., an electronic device configured to accept data, perform prescribed mathematical and logical operations at high speed, and output the results of these operations), such as, for example, but not limited to, a personal computer, a laptop computer, a palmtop computer, a notebook computer, a desktop computer, a workstation, a server, smartphone or any combination of the foregoing, or the like. The RU 150 may further include a telephone console, a telephone, a mobile telephone, a cellular telephone, an SDR, or the like, which may be capable of bidirectional communication with, e.g., the transceiver 120 and/or FM communicator 115. The RU 150 may be configured to receive fall event data from the transceivers 120 that is associated with one or more users 110. The fall event data may include, for example, date data, time data, current location data (e.g., real-time global positioning system (GPS) data, or the like), and the like. The fall event data may be received and reproduced as an audio/visual signal by the RU 150, such as, e.g., a voice message, a video message, or the like. The RU 150 may store the fall event data in the database 160 for each user 110. Further, the RU 150 may be configured to query the database 160, which may be internal, or external to the RU 150, for user data associated with a particular user 110. The user data may include, for example, but is not limited to, a name, an address, a telephone number, an email address, a current location, age, gender, current health conditions, allergies, family member name(s), in-case of emergency contact information, or the like. The RU 150 may be configured to, for example, dispatch emergency personnel to the user's 110 location based on the user data retrieved from the database 160.

The server may include, for example, any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

The database 160 may include, for example, any combination of software and/or hardware, including at least one application and/or at least one computer. The database 160 may include a structured collection of records or data organized according to a database model, such as, e.g., but not limited to at least one of a relational model, a hierarchical model, a network model or the like. The database 160 may include a database management system application (DBMS) as is known in the art. The at least one application may include, but is not limited to, for example, an application program that can accept connections to service requests from clients by sending back responses to the clients. The database 160 may be configured to run the at least one application, often under heavy workloads, unattended, for extended periods of time with minimal human direction.

The network 140 may include, but is not limited to, for example, at least one of the Internet, a local area network (LAN), a wide area network (WAN), a metropolitan area network (MAN), a personal area network (PAN), a campus area network, a corporate area network, a global area network (GAN), a broadband area network (BAN), a cellular network, or the like, or any combination thereof, any of which may be configured to communicate data via a wireless and/or a wired communication medium.

Any one or more of the elements in the FM system 100, including, e.g., the FM communicator 115, transceiver 120, access point 130, network 140, RU 150 or database 160 may be configured to communicate over a communication media that may include, for example, wired and/or wireless communications links, such as, for example, any one or more of: a satellite communication link, a cellular communication link, a radio frequency (RF) communication link, an infrared (IR) communication link, an optical communication link, or the like, without limitation. The RF communication link may include, for example, WiFi, WiMAX, Bluetooth, or the like.

The FM communicator 115 may be configured to generate and process fall status data, which may then be conveyed (or communicated) to one or more of the transceivers 120. Each transceiver 120 may then relay (or communicate) fall event data to, for example, the RU 150, which may be addressed based on a contact list stored in the transceiver 120. The FM communicator 115 may include various combinations of inertial sensors, such as, for example, but not limited to, tri-axial accelerometers, high-sensitivity pressure sensors (or ultra sensitive pressure sensors), and the like, to reliably detect both "hard" and "soft" falls, near falls and stumbles or gait changes, even when the sensors may be located on an extremity of a rigid body or a user 110 being monitored.

Figure 2:
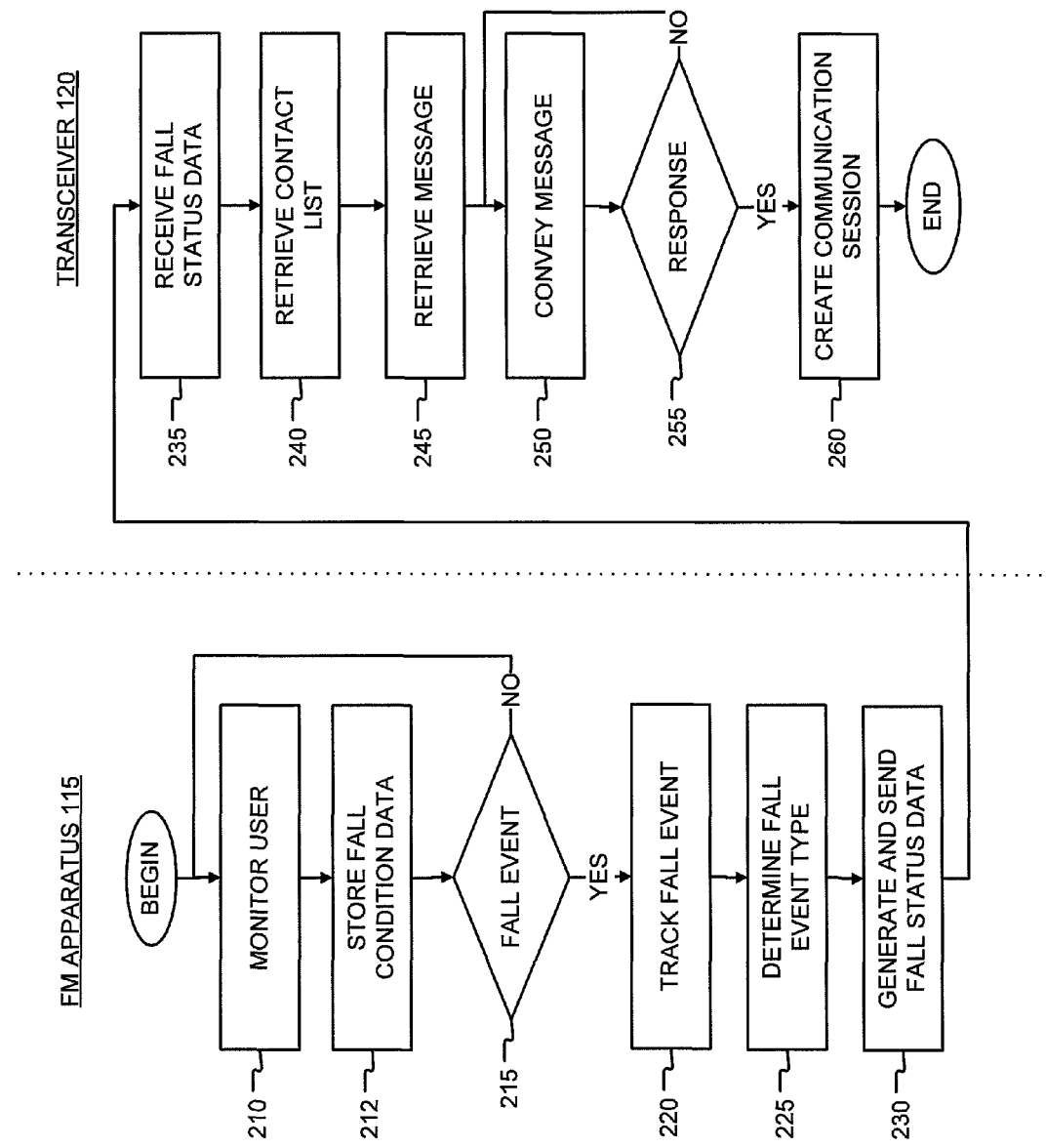
FIG. 2 shows an example of a fall monitoring process, according to principles of the invention.

FIG. 2 shows an example of a fall monitoring process, according to principles of the invention. Referring to FIGS. 1 and 2, the process may begin, for example, when the FM communicator 115 is affixed to the user 110, or when the FM communicator 115 is actuated (such as, e.g., via an ON/OFF switch, or by providing power to the FM communicator 115). Once powered on, the FM communicator 115 may monitor the orientation and movement of the user 110 (Step 210). It is noted that if two or more FM communicators 150 are used for monitoring, data (including fall condition data) from the FM communicators 150 may be synchronized prior to the start of monitoring and data collection, by using, for example, a USB-based multi-device docking station (not shown), which may be located in the transceiver 120.

Based on the monitoring, the FM communicator 115 may generate orientation data, translation movement data, rotational movement data, height data, height change data, time data, date data, location data, biometrics data, and the like, and store the data as fall condition data in an internal storage (Step 212). The fall condition data may be analyzed and detected for a fall event (Step 215) or other body orientation condition. In, fall event detection, algorithms may be used, which are based on a combination of: (a) unilateral (or, if necessary, bilateral) acceleration profiles measured, e.g., at the wrists; (b) impact accelerations measured, e.g., at the wrist(s); (c) sudden measured changes in altitude (barometric pressure); (d) a period of inactivity following a fall event; and/or (e) relative change in wrist(s) orientations following an ostensible fall event. Near-fall event detection algorithms may be also used, which are based on bilateral (or, if acceptable, unilateral) perturbation recovery reactions measured, e.g., at the wrist(s) and/or multifactorial combination of the wrist inertial, altimetry, and temporal feature characteristics.

Appropriate criteria and corresponding threshold values may be identified to enable accurate and reliable discrimination of both fall and near-fall events from other ADL. The algorithm that may be used to detect falls may nominally be based on unilateral triaxial accelerometer and altimeter data measured, e.g., on either wrist. The algorithm that may be used to detect near-fall events may ostensibly be based on bilateral triaxial accelerometer data measured on both wrists. In implementing a practical fall or near-fall detection algorithm, both false positives and false negatives should be avoided. For example, there are many ADL (e.g., walking, climbing stairs, and the like) that have significant acceleration components, but which do not represent falls or near-fall events. Additionally, bumping of the body (e.g., arms and torso) into objects and other people is also a common part of everyday life. Furthermore, changes in wrist orientations occur regularly in speaking, sitting, lying down, getting up, and the like. To determine fall and near-fall events, the concurrent occurrence of multiple qualifying criteria may be monitored. Various inertial "features" may be measured on the wrists that are likely to be useful in detecting and discriminating falls and near-falls from ADLs.

The following unilateral fall detection relationship (1) may be a useful starting point:

$$|a|=(a_x^2+a_y^2+a_z^2)^{1/2}>0.46 \text{ m/s}^2, \quad (1)$$

where $a_x$, $a_y$, and $a_z$, represent translational accelerations of the FM communicator 115 in the world coordinate system (x, y, z). In this regard, the acceleration vector magnitude is independent of the orientation of the FM communicator 115, and, therefore, the user 110. An integrated acceleration vector magnitude with the Earth's static gravitational acceleration, g, removed may be represented by the following equation (2):

$$v_1 = \int (a_x^2+a_y^2+a_z^2)^{1/2} dt \leftarrow 1.72 \text{ m/s}, \quad (2)$$

where $v_1$ is a dynamic velocity and t is time. Although this approximation is independent of wrist orientation, it may be correct for vertical movements. The norm of the integrated acceleration calculated for each axis separately, with the Earth's static gravitational acceleration contribution removed, may be expressed by the following equation (3):

$$v_2 = (\int a_x^2 dt + \int a_y^2 dt + \int a_z^2 dt)^{1/2} - \int g dt \leftarrow 2.62 \text{ m/s}, \quad (3)$$

where $v_2$ is the norm of the integrated acceleration calculated for each axis separately and $\int g dt$ is the Earth's static gravitational acceleration contribution. This approximation is not independent of, e.g., wrist orientation and, therefore, is a good approximation if, e.g., the wrist does not rotate during a fall.

An impact event, which may be defined based on the differential acceleration vector magnitude, $d|a|/dt$, may then be detected within three seconds (3 s) of a detected high-speed event towards the ground. If an above-threshold impact event is detected, forty seconds (40 s) of the minute (1 min) following the impact may be characterized by inactivity, which may be defined as a ceiling on the integrated acceleration vector magnitude, $\int |a| dt$. In this regard, the monitoring samples may be contiguous or non-contiguous. For hard or soft falls, periods of inactivity following a detected event may be determined as an actual fall and, if the inactivity persists (e.g., for greater than or equal to 1 min.), the user 110 may be determined to be potentially unconscious. The FM communicator 115 may detect a subsequent change in orientation of, e.g., the wrist(s) following a fall as additional inertial feature for use in detecting falls. For example, the subsequent change may include a difference between the mean accelerations presently measured on each axis and those measured two seconds prior to the impact event.

The near-fall event detection algorithm may nominally be based on the inertial bilateral perturbation recovery reaction measured, e.g., at the wrist(s) of the user 110 as a condition for identifying near falls. In this regard, changes in wrist orientations that might occur in speaking, sitting, lying down, getting up, shaking drinks, or the like, would not trigger a near-fall event detection.

The performance of the fall and near-fall event detection algorithms may be evaluated independently. Falls may be defined as events that occur in response to translational perturbations in the plane of the platform in which falls are allowed and which actually result in a fall (e.g., part of the user's 110 torso is in contact with a horizontal plane). Near-fall events may include all non-fall events.

Referring to the process shown in FIG. 2, if a fall event is detected ("YES" at Step 215), then the fall event is tracked (Step 220), otherwise the FM communicator 115 may continue to monitor the orientation and movement of the user 110 ("NO" at Step 215, Step 210). In tracking the fall event (Step 220), the FM communicator 115 may continuously (or discretely, such as, e.g., at predetermined intervals) sense the orientation and movements of the user 110.

On the basis of the tracked fall event (Step 220), the FM communicator 115 may determine a fall event type (Step 225). The fall event type may include, for example, a "soft" fall event, a "hard" fall event, a fall event, a near-fall event, a level of susceptibility to a fall, or the like. The threshold values for "soft" or "hard" may be set, for example, at the original equipment manufacturer (OEM), or provided post-manufacturing. The threshold values may be based, for example, on a degree of motion over a predetermined period of time. For example, a "hard" fall event may be determined when, for example, the FM communicator 115 experiences a three-foot drop in a fraction of a second; and a "soft" fall event may be determined when, for example, the FM communicator 115 experiences a three-foot drop over a period of three or more seconds. It is noted that the foregoing threshold values are merely provided to illustrate examples of threshold values for "soft" and "hard" falls and are in no way limiting. Furthermore, the range of fall event values is in no way limited to "soft" and "hard" falls, but, instead, may have any number of threshold values for the fall event, including, for example, but not limited to, a "very soft" fall, a "medium" fall, a "very hard" fall, and the like.

The FM communicator 115 may generate fall status data based on the determined fall event type and send the fall status data to a transceiver 120 (Step 230). The transceiver 120 may receive the fall status data from the FM communicator 115 (Step 235). The transceiver 120 may retrieve a contact list from an internal storage and select an address from the list based on the fall status data (Step 240). The contact list may include, for example, a prioritized listing of names, telephone numbers, addresses, or the like. The contact list may be prioritized based on a particular fall event type, a particular time of day, a particular date, or the like, to maximize the probability of reaching a person who may be able to assist the user 110.

The transceiver 120 may further retrieve a message from the internal storage based on the fall status data received from the FM communicator 115 and/or the particular contact selected from the contact list (Step 245). In this regard, a plurality of messages may be stored in the internal store, each of which may be associated with a particular contact and/or fall event type. Then, the retrieved message may be conveyed to the selected contact (Step 250). In this regard, the message may be conveyed as a visual message (e.g., a text message, an instant message, an SMS message, an email message, or the like), as an audio message (e.g., a telephone message, an audio file message, or the like), a combination of a visual message and an audio message, or the like.

After the message is conveyed to the contact (Step 250), the transceiver 120 may detect for a response message, such as, for example, a visual message, an audio message, or the like (Step 255). If a response message is not detected, e.g., within a predetermined amount of time (e.g., two seconds) ("NO" at Step 255), then the transceiver 120 may select another contact (or record) from the contact list and convey a message to the newly selected contact (Step 250). If, however, a response message is detected ("YES" at Step 255), then a communication session may be created between the transceiver 120 and the contact (e.g., the RU 150, shown in FIG. 1) (Step 260). For example, a speaker phone may be activated to open audio and/or visual communication between the user 110 and the contact.

According to a further aspect of the invention, a computer program may be provided on a computer readable medium (such as, e.g., a random access memory (RAM), a read only memory (ROM), a flash drive, a hard drive, a CD-ROM, a DVD-ROM, or the like), which, when executed on a computer, may cause the computer to carry each of the Steps 210 through 260 in FIG. 2. The computer readable medium may include a plurality of sections (or segments) of code, including a section (or segment) of code associated with each of the Steps 210 through 260.

Figure 3:
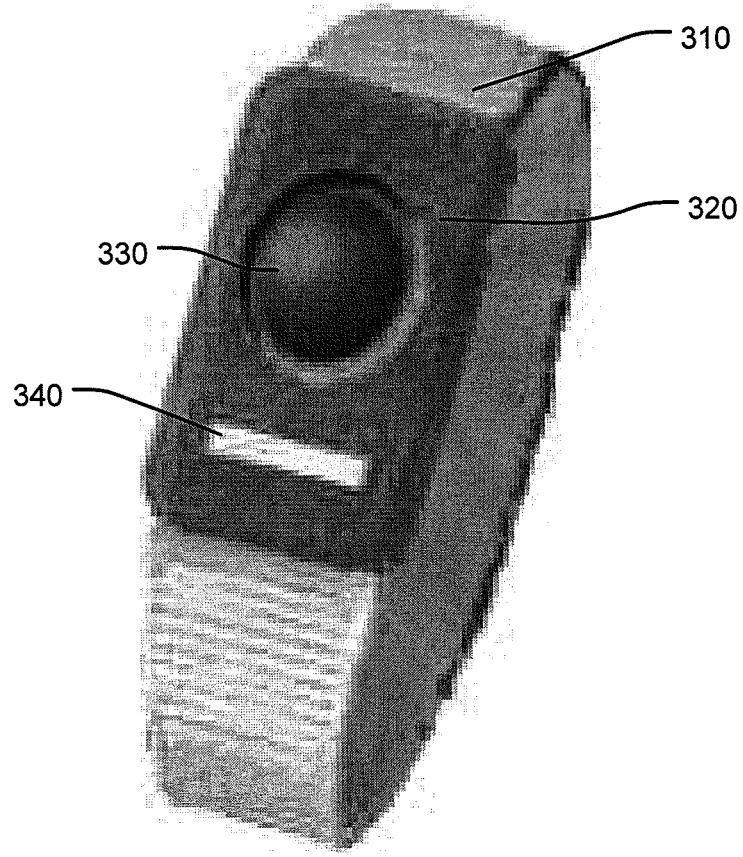
FIG. 3 shows an example of a fall monitoring (FM) communicator, according to principles of the invention.

FIG. 3 shows an example of an FM communicator 115, according to principles of the invention, which may be worn on the wrist or forearm of the user 110 (shown in FIG. 1). As seen, the FM communicator 115 may include a band (e.g., a wristband) 310 that may be securely affixed to a wrist or forearm of the user 110, as well as an FM communicator (FMC) module 320. The band 310 may include, for example, a hook and loop material (e.g., Velcro, or the like). The FMC module 320 may include one or more sensors (not shown) configured to monitor date, time, location, biological functions (or biometrics) (such as, e.g. heart rate, blood pressure, body temperature, body perspiration, or the like), and a power supply (e.g., a battery, a rechargeable battery, or the like). The FMC module 320 may be completely covered in, e.g., polyethylene shrink wrap to isolate the electronics. A slot may be provided in the shrink wrap to enable battery replacement. The FMC module 320 may further include one or more sensors configured to monitor the level of activity (or lack of activity) in monitoring, detecting and determining a fall status condition (such as, e.g., a fall, a near fall, a "hard" fall, a "soft" fall, or the like). The fall status information collected by the FMC module 320 may be stored in an internal storage and transmitted via, e.g., wireless communication to a transceiver 120 and/or RU 150 (shown in FIG. 1). The FMC module 320 may provide for an autonomous assistance notification system if a fall or near-fall event occurs while the FMC module 320 is being used to track health, safety or the state of a monitored user 110. Similarly, the near fall data can be analyzed to note trends to, e.g., take preventive steps to minimize or prevent the occurrence of a "hard" fall.

The FMC module 320 may be configured to detect changes in the height of the user 110, which may be used in conjunction with information detected by the inertial sensors to provide information on the translational and rotational movement of the body of the user 110, and may be used to develop a representation in three dimensions of the state of the body of the user 110 at any moment in time and, therefore, relay a notification to the transceiver(s) 120 when any change or lack of change in state occurs. For example, hard falls may be measured by monitoring forearm triaxial accelerometer profiles (e.g., free fall), high-g impacts, and/or a relatively rapid change in height (e.g., 3 feet occurring over a few seconds, or less) based on a high-sensitivity pressure sensor (altimeter) incorporated within the FMC module 320. Further, soft falls, in which an individual might, for example, "crumple" to the floor, whether or not he/she holds onto anything (e.g., furniture, a railing, or the like), may be detected reliably based on a relatively rapid change in height, as discussed above, followed by an interval (e.g., 2 minutes) of immobility. In the latter instance, the user 110 may have lost consciousness. If the user 110 remains conscious, he/she can initiate or cancel a personal emergency alert via the button 340. Requiring a period of immobility following a rapid change in height (pressure) may eliminate potential false alarms due, for example, to rapid descent of stairs, riding in an elevator, and raising and lowering one's arms (e.g., during exercise).

The FMC module 320 may be configured to be highly sensitive to translational and/or rotational motions and reactions, which are typically the most characteristic of falls and near fall events. For example, the FMC module 320 may be tuned to the particular aspects of such events as, for example, but not limited to, a recovery arm motion that occurs when the user 110 falls. In this regard, the FMC module 320 may include one or more accelerometers or gyroscopes (not shown) that may provide information on the movements, positions, and orientation of the user 110 in a three dimensional space. These devices may be configured to quickly and accurately measure additional changes in the orientation of the body of the user 110, supplemented by the height and changes in height information provided by the one or more ultra-sensitive pressure sensors.

As discussed above, a single FM communicator 115 may be sufficient for accurate detection of fall events. However, one or more additional FM communicators 115 may provide more accurate detection, including more accurate detection of near-fall events. In the latter case, a pair of FM communicators 115 may be bilaterally affixed to the wrists of the user 110 (shown in FIG. 1). Each of the FM communicators 115 may be configured to exchange data wirelessly (or wired) and function together to reliably discriminate fall event types from other activities of daily living (ADL). Upon detection of a fall, the FM communicator 115 may automatically summon assistance by sending, e.g., a radio signal to the transceiver 120 (shown in FIG. 1), which may comprise a telephone console unit (with built-in speakerphone), to deliver a message to a prioritized list of caregivers and ensure that it is received by a human being and not an answering machine. The fall condition type information, including fall and near-fall event information, time of day, maximum acceleration vector magnitude, and the like, may be logged in the transceiver 120 for each detected event. The fall condition type information may also be logged in the FM communicator 115, the RU 150 or the database 160.

As seen in FIG. 3, the FM communicator 115 may comprise a single large recessed actuator button 330 on its face that can also be used to initiate a personal emergency alert call or to cancel an alert call that is in progress. The FM communicator 115 may be configured to vibrate and/or emit an audio/visual signal to alert the user 110 of a call in progress. In this regard, the FM communicator 115 may comprise a display 340 (such as, e.g., an LED, LCD, or the like), which may display a message (e.g., a red light when an emergency call is placed to the transceiver 120, a green light during non-fall events, or the like). The FM communicator 115 may be configured to be reversible to prevent access to the actuator button 330 by a cognitively-impaired user 110, who might press the actuator button 330 without cause.

Furthermore, by positioning the FM communicator 115, including the FMC module 320, on, e.g., an extremity of the user 110 that is often employed in the maintenance of balance (e.g. the wrist of a human, the wrist of a robot, the neck of a horse, or the like), the inertial motions (such as, e.g., rapid changes in altimeter and/or g-force measurements, and/or high-g impacts) associated with the user 110 may be measured and determined and can provide for sensitive measures of hard, soft and near-fall events. For some embodiments of the invention, it may be preferred to employ bilateral devices (e.g., an FM communicator 115 on each wrist of the user 110) to improve the ability to discriminate between a wide range of motions a user 110 may execute during normal activities of daily living (ADL). As an example, a firefighter 110 may routinely jog up stairs, an action that may be accompanied by a swinging arm motion that the FMC module 320 might need to be tuned into in order to note the fairly repetitive motion as normal. The kinematic features that may be characteristic of near-fall events, as well as hard and soft fall events, may be reliably measured and incorporated into the FMC module 320 to track, monitor and/or autonomously signal any type of fall event. In this regard, the FMC module 320 may include fuzzy logic, neural networks, or other known artificial intelligence (AI) systems.

Figure 4:
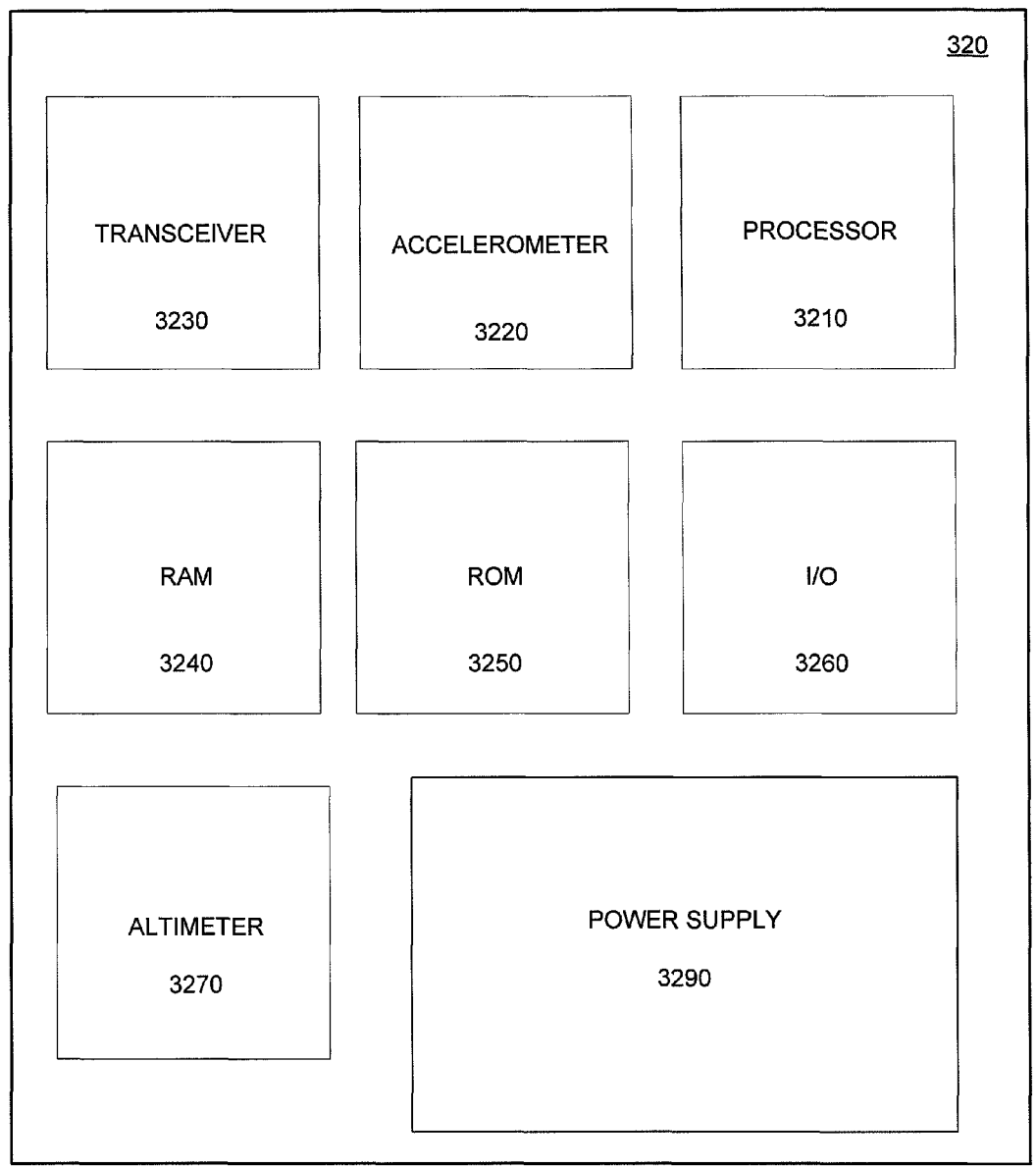
FIG. 4 shows an example of a fall monitoring communicator (FMC) module, according to principles of the invention.

FIG. 4 shows an example of an FMC module 320, according to principles of the invention. As seen in FIG. 4, the FMC module 320 may comprise a processor 3210, an accelerometer 3220, a transceiver unit 3230, a RAM 3240, a ROM 3250, an input/output (I/O) interface 3260, an altimeter 3270, and a power supply 3290. The FMC module 320 may be, for example, encapsulated in a waterproof, hermetically sealed housing (not shown). The transceiver unit 3230 may include, for example, a wireless transceiver chip, such as an IEEE 802.15.4, ZigBee chip, or the like.

The processor 3210 is configured to accept data, perform prescribed mathematical and logical operations at high speed, and output the results of these operations. The processor 3210 may control the operation of the various components of the FMC module 320, including task management and data handling. Further, the processor 3210 may include, for example, a Texas Instruments MSP430F4794 16-bit ultra-low-power mixed-signal microcontroller that has about 60 KB of non-volatile Flash ROM (program memory) and about 2.5 KB of volatile static RAM (scratchpad memory). The processor 3210 may further include multiple timers, multiple (e.g., four) 16-bit analog-to-digital (A/D) converters, and multiple (e.g., two) high-speed serial communication controllers, at least one of which may be used for uploading data to a computer off line or the transceiver 120 (shown in FIG. 1). The processor 3210 may include multiple (e.g., five) power-saving modes that may be ideal for battery-powered applications (e.g., a "standby" mode in which the current draw may be about 1.1 μA and which can be used between sampling instants, as the "wake-up" time from standby mode is less than 6 μs). The processor 3210 may be configured to run at a frequency of, for example, about 1 MHz and draw less than about 0.62 mW of power. The three accelerometer channels from the accelerometer 3220 may be sampled at a rate of, for example, about 256 Hz to ensure capture of all dynamic motions of potential interest. Similarly, the data from the altimeter 3270 may also be sampled at, for example, about 256 Hz and the samples averaged over approximately 1-s intervals (based on a sliding window) to reduce the FM communicator 115 noise floor and enable detection of transient changes in atmospheric pressure.

The accelerometer 3220 may be configured to monitor and measure orientation and movement of the FMC module 320 in six degrees of freedom (6-DOF) and generate inertial data in real time, which may be used to reconstruct and animate fall events in three-dimensional space. The accelerometer 3220 may include, for example, a single triaxial accelerometer chip such as, e.g., an Analog Devices ADXL330 IC. The accelerometer 3220 may be configured to sense both dynamic acceleration (motion) and static acceleration (gravity), within, for example a dynamic range of about ±3.0 g, which is sufficient for capturing the motions of interest. The accelerometer 3220 may be configured to use about 0.32 mW of power during operation. The output from the accelerometer 3220 may be digitized using, for example, a subset (e.g., three of the four 16-bit A/D converter channels) of the multiple A/D converter channels in the processor 3210, each of which may provide a resolution of, for example, about 45.8 μg.

The transceiver 3230 may be configured to maintain synchrony of data sampling with another FMC module 320, such as, e.g., for bilateral monitoring to detect near-fall events. The data may be exchanged between the plural FMC modules 320 (via the transceiver units 3230) to provide accurate decision-making regarding fall events, and to initiate fall and personal alerts by communicating with the transceiver 120 (shown in FIG. 1). In this regard, wireless communication repeater units (not shown) may be included in the FM system 100 (shown in FIG. 1), including, for example, AC-adapter Bluetooth (IEEE 802.15.1), or ZigBee wireless communication repeaters, or the like. For example, transmission distances for ZigBee transceivers can range up to 100 m, depending on power output and environmental characteristics. The transceiver 3230 may operate, for example, in a 900 MHz band.

The RAM 3240 may be configured to temporarily store detected fall condition data, such as, for example, when the user 110 is out of range of the transceiver(s) 120. The RAM 3240 may include, for example, a non-volatile Flash RAM chip, which may be used to store continuous accelerometer and atmospheric pressure data sensed by, for example, the accelerometer 3220 and altimeter 3270. The RAM 3240 may be configured to continuously collect data on, for example, four channels at a rate of, for example, about 256 Hz. In this regard, the fall condition data may be uploaded from the FMC module 320 to the transceiver 120 at predetermined fixed (or variable) intervals (such as, e.g., every 30 s, every 1 min, every 5 min, every 10 min, or the like), when a fall event is detected (e.g., "YES" at Step 215, shown in FIG. 2), or when the user 110 is back within range of the transceiver(s) 120. The fall condition data may be uploaded to the transceiver 120 (or a personal computer (not shown)) via wireless communication or by placing the FM communicator 115 in, for example, a docking station (not shown), which may be in the transceiver 120. Further, the fall condition data in the RAM 3240 may be synchronized with fall condition data in a corresponding RAM (not shown) of another FM communicator 115, for example, before a new data collection period begins.

The ROM 3250 may be configured to store long term data as well as executable code, which may be executed, for example, by the processor 3210.

The I/O interface 3260 may facilitate exchange of data and control signals between, for example, a user interface (e.g., the button 330, shown in FIG. 3), a graphic user interface (e.g., the display 340), or the like, and the various components in the FMC module 320.

The altimeter 3270 may include, for example, a high-sensitivity, temperature-compensated, calibrated pressure sensor (e.g., Freescale MP3H6115A, Freescale MPX4115A, or the like), which may be able to discriminate relatively small differences in elevation. The altimeter 3270 may be configured to measure absolute pressures over, for example, a range of about 150 hPa to about 1150 hPa. It is noted that atmospheric pressure close to the Earth's surface decreases quasi-linearly with altitude at a rate of 0.12 hPa/m. To take advantage of the full sensitivity of the altimeter 3270 in the atmospheric pressure range of interest, the output may be clamped using, e.g., a potentiometer, as shown in FIG. 5B, so that an output of zero may correspond to about 950 hPa (in the example shown in FIG. 5B) which may provide a weather-related low-pressure floor below the average barometric pressure of, for example, 983 hPa (in the example shown in FIG. 5B) for certain geographic locations where the average elevation may be 850 feet above sea level. Further, an altimeter 3270 output of about 5 V may be set to correspond to about 1150 hPa, which exceeds the highest global barometer reading recorded to date, i.e., 1083.3 hPa.

The power supply 3290 may include a disposable or rechargeable power source, such as, e.g., a battery. For example the power supply 3290 may include one or more 3V CR1225 150 mAh lithium coin batteries.

Figure 5A:
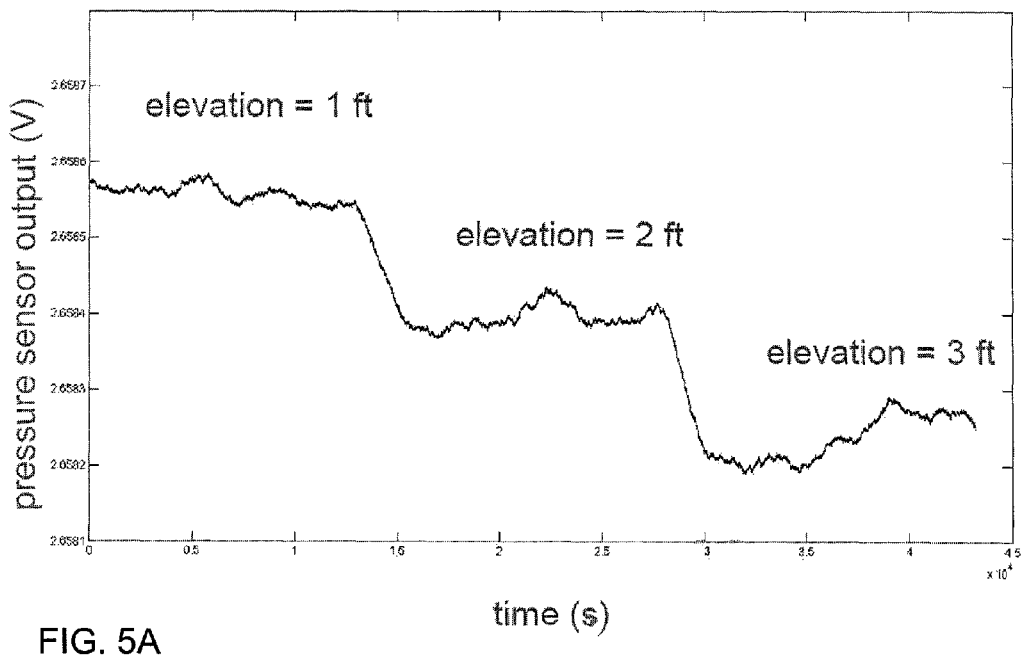
FIG. 5A illustrates a chart showing examples of output pressure values for certain elevation values.
Figure 5B:
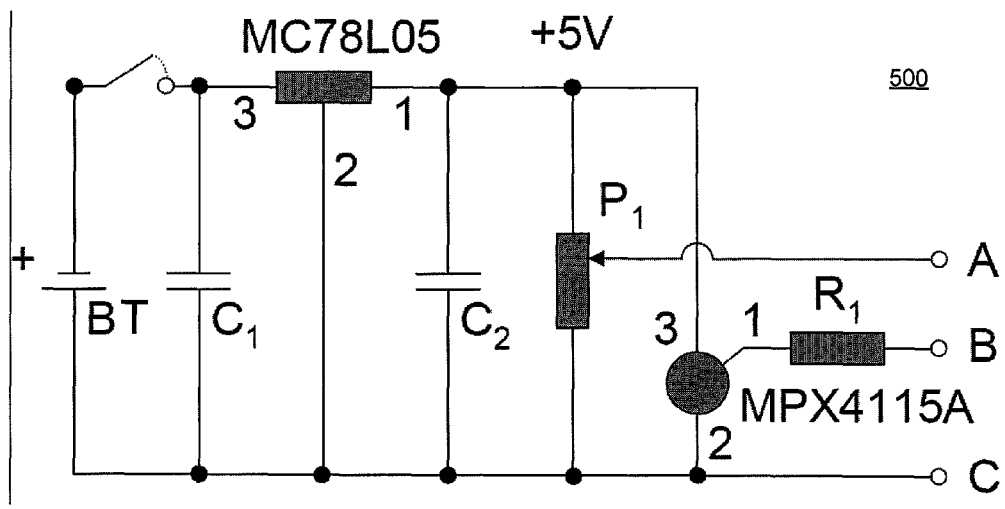
FIG. 5B shows an example of an ultra-sensitive pressure sensor that may be used in the FM communicator of FIG. 3, according to principles of the invention.

FIG. 5A illustrates a chart showing examples of pressure value data that may be output by the altimeter 3270 using, e.g., a Freescale MP3H6115A sensor, over a range of three elevation values (i.e., elevation=1 ft, 2 ft and 3 ft). The Freescale MP3H6115A sensor may have a sensitivity of about 2.7 mV/hPa. As seen, the difference in the altimeter 3270 outputs at elevations of 1 and 3 feet may be approximately 0.3 mV, which represents a change in pressure of about 0.3 mV/2.7 mV/hPa=0.1 hPa for, e.g., the Freescale MP3H6115A sensor, which is close to an expected value of 0.07 hPa for a change in elevation of 2 ft near the Earth's surface. Relatively rapid changes in elevation of about 2 ft may be detecting based on, e.g., the data shown in FIG. 5. It is noted that the altimeter 3270 may include, e.g., the Freescale MPX4115A sensor, or the like, which has a sensitivity of about 4.59 mV/hPa.

FIG. 5B shows an example of altimeter 500 that may be used in (or as) the altimeter 3270 of FIG. 4, according to principles of the invention. The altimeter 500 may include a power supply BT (e.g., a 9V type 6LR610 battery), a first capacitor C1 (e.g., 0.33 μF), a second capacitor C2 (e.g., 0.01 μF), a potentiometer P1 (e.g., 10 turns potentiometer, 20 kΩ, 0.5 W), a voltage regulator (e.g., 5V MC78L05), a pressure sensor (e.g., MPX4115A), and a protecting resistor R1 (e.g., 750 Ω/0.1 W). The altimeter 500 may be configured as shown in FIG. 5B, including terminals A, B, C.

Figure 6:
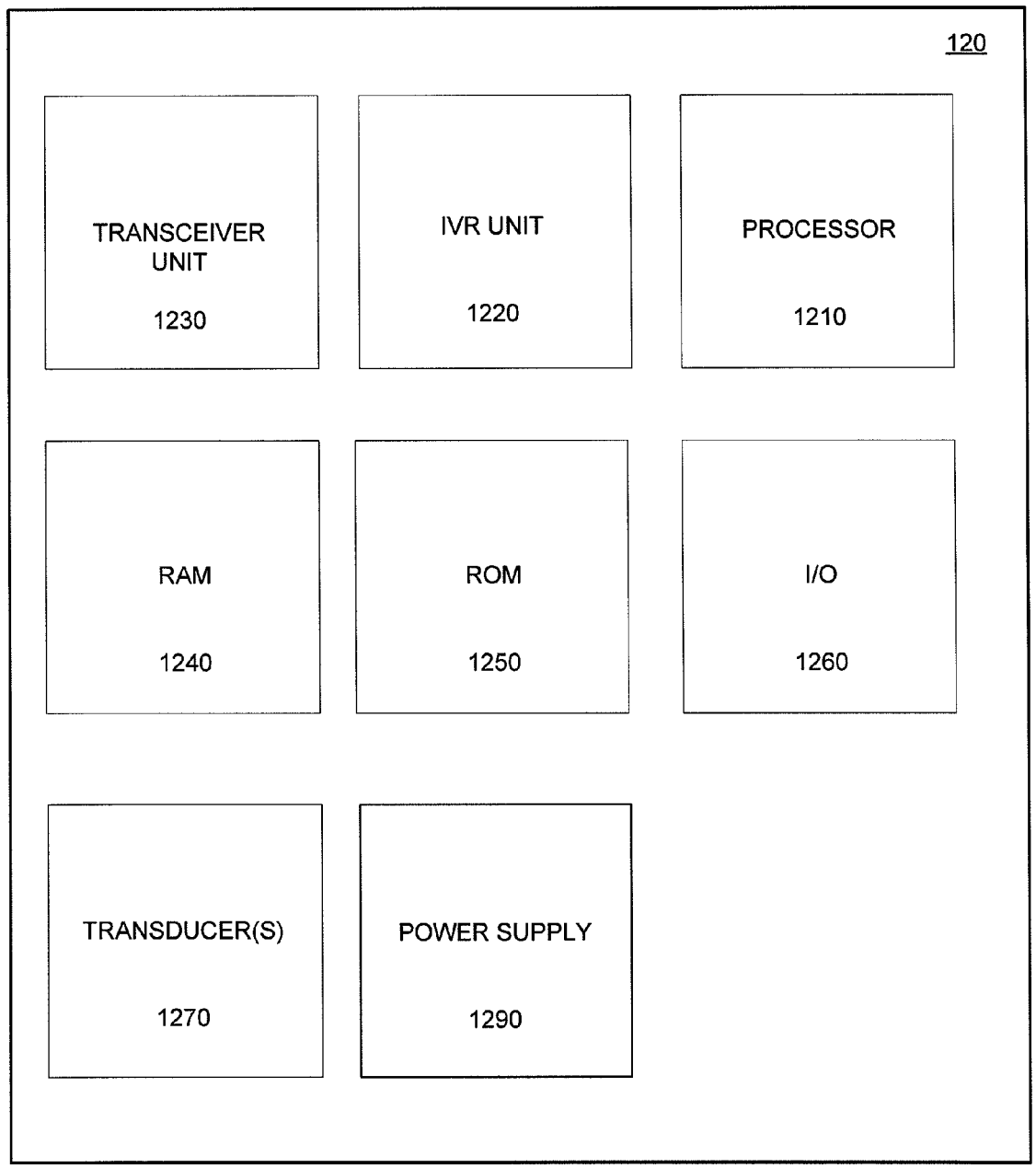
FIG. 6 shows an example of a transceiver that may be used in the FM monitoring system of FIG. 1, according to principles of the invention.

FIG. 6 shows an example of a transceiver 120, according to principles of the invention. The transceiver 120 may be portable or stationary. As seen in FIG. 6, the transceiver 120 may comprise a processor 1210, an interactive voice response (IVR) unit 1220, a transceiver unit 1230, a RAM 1240, a ROM 1250, an input/output (I/O) interface 1260, one or more transducers 1270 and a power supply 1290. The transceiver 120 may further comprise an antenna (not shown).

The processor 1210 is configured to accept data, perform prescribed mathematical and logical operations at high speed, and output the results of these operations. The processor 1210 may control the operation of the various components of the transceiver 120, including task management and data handling.

The IVR unit 1220 may be configured to synthesize a voice message that, for example, identifies the nature of a call. The IVR unit 1220 may ask, for example, emergency call recipients to acknowledge receipt of a call by saying a particular command, pressing a key on a touch-tone telephone, responding with an audio/visual message, or the like. Upon receiving an acknowledgement, a communication session may be established between the transceiver 120 and the call recipient (e.g., RU 150, shown in FIG. 1). In this regard, the transducer 1270, which may include a speakerphone and a microphone, may be activated to allow for bidirectional communication between the user 110 and the call recipient. By requiring acknowledgement of receipt of the message call from the transceiver 120 may ensure that the emergency calls are received by a human being rather than an answering machine.

The transceiver unit 1230 may include, for example, a telephone modem, a radio frequency (RF) transmitter and receiver, and the like, to enable bidirectional communication between the transceiver 120 and the FM communicator 115 and/or the RU 150 (shown in FIG. 1). The transceiver unit 1230 may include, for example, a wireless transceiver chip, such as an IEEE 802.15.4, ZigBee chip, or the like. The transceiver unit 1230 may be configured to receive data, including fall condition data, as well as control signals from the FM communicator 115. The transceiver unit 1230, under control of the processor 1210, may be configured such that failure of any party on the call list to acknowledge an emergency call will cause a call (e.g., a 911 call) to be placed to emergency personnel, who can then talk to the user 110 after acknowledging the call and/or using the telephone number of the user 110 (e.g., obtained via caller ID) to determine the address to which to send help. The user 110 may have the option of canceling any call in progress by manipulating a user interface (e.g., the large recessed actuator button 330, shown in FIG. 3) on the FM communicator 115. The same user interface may be used to initiate a personal emergency alert and to cancel an emergency alert that is in progress. The transceiver 120 may be configured to be as easy to set up as a conventional telephone answering machine.

The RAM 1240 may be configured to temporarily store detected fall condition data, one or more contact lists, and the like. The fall condition data may be downloaded from the FM communicator 115 at predetermined intervals, when the user 110 is back within range of the transceiver(s) 120, or, when a fall event is detected.

The ROM 1250 may be configured to store long term data as well as executable code, which may be executed, for example, by the processor 1210.

The I/O interface 1260 may facilitate exchange of data and control signals between, for example, a user interface (e.g., alphanumeric keypad, or the like) (not shown), a graphic user interface (e.g., a touch-screen display, or the like) (not shown), or the like, and the various components in the transceiver 120.

The transducer(s) 1270 may include, for example, but not limited to, a speaker (not shown), a microphone (not shown), a display (not shown), and the like.

The power supply 1290 may include an input for an alternating (AC) or direct current (DC) power source, such as, e.g., household electricity; and/or a disposable or rechargeable power source, such as, e.g., a battery.

Figure 7A:
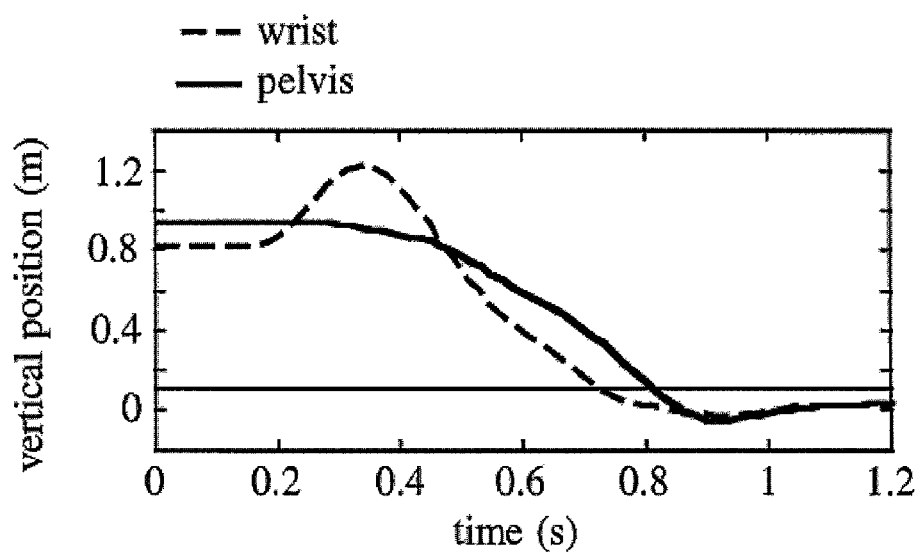
FIG. 7A shows a chart of change in position of wrist and pelvis in response to a forward translational perturbation of the lower limbs initiated at time zero that results in a fall.
Figure 7B:
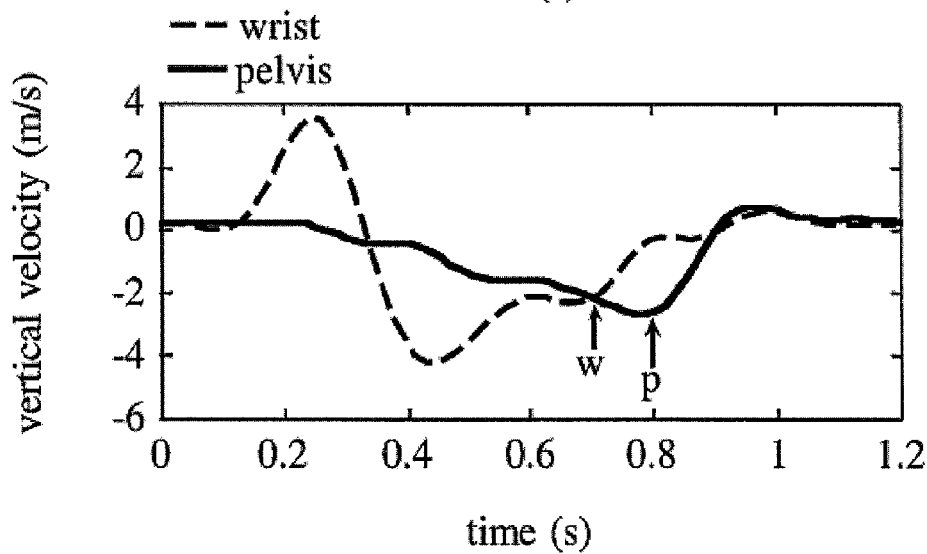
FIG. 7B shows a chart of change in vertical velocity of wrist and pelvis in response to a forward translational perturbation of the lower limbs initiated at time zero that results in a fall.

FIGS. 7A and 7B show changes in position and velocity, respectively, of wrist and pelvis in response to a forward translational perturbation of the lower limbs initiated at time zero that may result in a fall. It is now widely appreciated that reactive balance control following external perturbations involves coordinated activation of musculature of the legs, torso, arms, and neck. Much of the recent research in the field of posture and balance in the context of postural stability has focused on the important role that the arms, in particular, play in the recovery response to unexpected perturbations. For example, arm movements can be employed as part of an active recovery strategy to avoid falling through the introduction of inertial effects (e.g., much as swinging of the arms is used for stabilization of the body during locomotion, or as a protective mechanism, absorbing impact and shielding the pelvis and head from high-speed impact, to avoid potential injury from a fall. As shown in FIGS. 7A, 7B, Hsiao and Robinovitch found, as discussed, for example, in Hsiao E T, Robinovitch S N, "Common protective movements govern unexpected falls from standing height," J Biomech, January 1998; 31(1):1-9, that a forward translational perturbation of the lower legs may lead to an immediate upward movement of the wrists to a maximum speed of 400 cm/s, followed by a rapid downward movement to a maximum speed of 400 cm/s, and a second upward dynamic acceleration in excess of 1 g that substantially reduces wrist speed just prior to impact (which occurred 90 ms before pelvis impact). Hsiao and Robinovitch observed that impacts occurred to both wrists in 93% of complete falls. The arm reactions that occur immediately following a perturbation of one or both lower limbs may be substantially faster than volitional arm movements, where for the latter, there may be an opportunity to pre-plan the movement. These reactions appear to reflect more than merely a "startle" response, since they are scaled to the magnitude of the perturbation. Older adults appear to rely more on arm reactions than young adults due to age-related deterioration in other postural control mechanisms.

Figure 8:
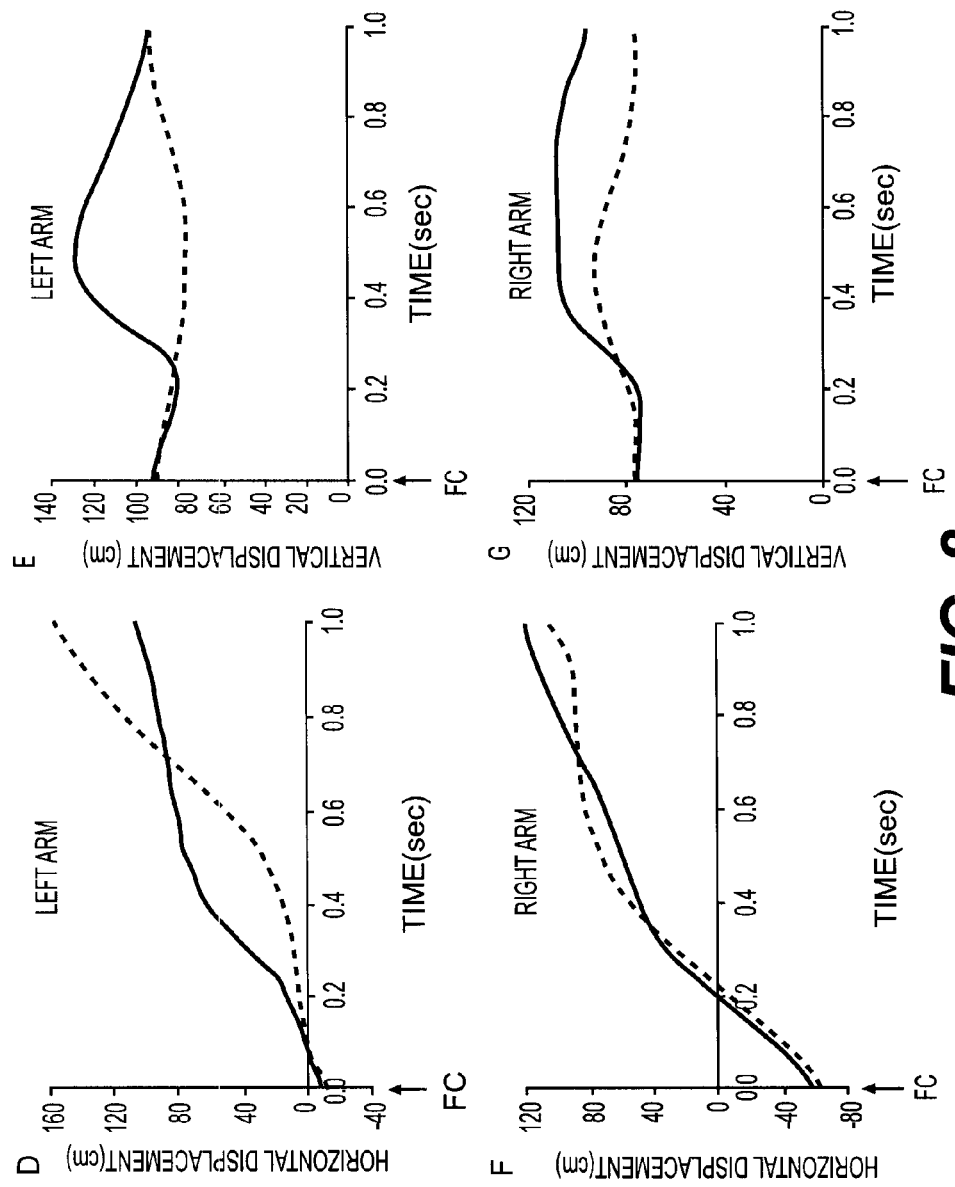
FIG. 8 shows charts D, E, F, G, showing forearm (wrist) horizontal and vertical trajectories during walking (dashed line) and unexpected slipping (solid line).

FIG. 8 shows charts D, E, F, G, showing forearm (wrist) horizontal and vertical trajectories during walking (dashed line) and unexpected slipping (solid line). In gait slipping experiments by Marigold et al. (e.g., as described in Marigold D S, Bethune A J, Patla A E, "Role of the unperturbed limb and arms in the reactive recovery response to an unexpected slip during locomotion," J Neurophysiol, April 2003; 89(4): 1727-37, Epub Dec. 11, 2002), it was found that the left and right deltoid muscles both activated within approximately 150 ms and were similar in timing to the responses of the unperturbed lower (leg) limb, indicating that a dynamic multi-limb coordinated strategy is employed by the central nervous system to control and coordinate the upper and lower limbs in reactive recovery responses to unexpected slips. Left forearm vertical and horizontal flexion/elevation speeds measured at the wrist in response to right foot slips may both peak at about 200 cm/s. Right forearm horizontal displacement may not be different from the unperturbed case, but right forearm vertical speed may reach about 200 cm/s. The changes in forearm speed, which may occur over an interval of approximately 200 ms, represents accelerations on the order of 1 g. In this case, a user 110 may be seen to move both arms rapidly in the same manner (flexion). Arm responses to translational platform perturbations in both the anterior-posterior and mediolateral directions from a standing posture in young and middle-aged users (e.g., age range: 23-48 years)

may result in bilateral elbow flexion and shoulder abduction, independent of perturbation direction. Elbow flexion angular speed may reach about 300 deg/s and shoulder abduction angular speed may reach about 80 deg/s. Deltoid muscle activation may be observed at about 90 ms, which is coincident with early muscle activation of the stabilizing ankle response. Bilateral arm responses may be scaled to the perturbation magnitude, but may move rapidly in the same direction (flexion).

It appears that older adults may be more likely than younger adults to initiate arm movements in response to translational platform perturbations. The timing and magnitude of shoulder muscle activations may be modulated according to the characteristics of the perturbation and even the earliest trajectory of arm motion may vary according to the direction of the perturbation. Although shoulder muscle activity may begin very early after perturbation onset, similar in timing to the ankle response, unlike the ankle muscles, arm and shoulder muscles may not be activated or involved in balancing prior to initiation of the perturbation. In response to sudden roll tilt of the lower legs from a standing posture using a multidimensional stance perturbation platform, initial arm roll movements (e.g., abduction and adduction) of elderly users (e.g., 60-75 years old) may differ from those of young (e.g., 20-34 years old) and middle-aged (e.g., 35-55 years old) users. In young and middle-aged users, initial arm roll movements may be in a direction opposite to the tilt (i.e., but in the same direction as the initial trunk roll recovery response). In elderly users, however, initial arm roll movements may be in the same direction as the tilt (i.e., which may also be in the same direction as trunk roll). Thus, whereas young and middle-aged users may adduct the down-hill arm and abduct the uphill arm relative to the trunk, elderly users may do the opposite: i.e., abduct the downhill arm and adduct the uphill arm. For roll tilts, therefore, users may move both arms rapidly in the same direction, either in the same or opposite direction as the platform tilt.

Independent of the arm movement direction relative to the trunk, all three groups of users may reach equivalent kinematic downhill upper-arm roll angular speeds of approximately 20 deg/s, just at different times (175-275 ms in the younger groups, 400-500 ms in the elderly group) and in different directions (adduction for the younger groups, abduction for the elderly group). These arm speeds may be measured on the upper aspect of the arm; due to its location near the non-pivoting end of a moment arm, wrist translational speeds may be several times greater than the upper-arm translational speeds.

In elderly users, whereas the downhill arm may achieve an abduction roll angle of about 3° to 4° relative to the trunk 700 ms after initiation of the perturbation (by which time the trunk velocity had stabilized), the uphill arm may achieve an adduction roll angle of about 2° to 3°.

The responses to multidimensional stance perturbations of users with Parkinson's disease may include sudden forward pitch perturbations of the lower legs, causing arm and trunk extension (backward pitching); conversely, sudden backward pitch perturbations of the lower legs may cause arm and trunk flexion (forward pitching). Responses in users with Parkinson's disease may be similar to those of users not having Parkinson's disease, but somewhat decreased in speed and peak displacement. Still, even in the slowest cases—Parkinson's disease users off their medication with pitch direction (backward pitch) perturbations—upper-arm motions may reach flexion speeds exceeding 12 deg/s, followed by extension speeds exceeding 14 deg/s. The same Parkinson's disease users off their medication may have an average extension speed in excess of 33 deg/s in response to forward pitching perturbations, very similar to users with Parkinson's disease on their medication. Parkinson's disease users may lack the normal graded arm pitch control for different amounts of backward pitch; in Parkinson's disease users, the arm activation may resemble a startle reflex, since the activation may not be scaled to the perturbation magnitude. Deltoid muscles responses may occur earlier in users with Parkinson's disease (on or off their medication) than in non-Parkinson's users, which is consistent with a startle response. For all pitch tilts, therefore, users with or without Parkinson's disease may have the following in common: all may move both arms rapidly in the same direction.

Referring back to FIG. 1, use of bilateral FM communicators 115 in the FM system 100 may enable the exploitation of bilateral forearm kinematic features that are characteristic of near-fall events, as well as fall events. The kinematics of instinctive bilateral arm reactions that occur in response to slipping and tripping events, especially in older adults, may be used to discriminate near-fall events from ADL. The specific recovery and/or protective reactions, which may have onset latencies that are as early as (or earlier than) those of the legs, may be generally dependent on the direction of the perturbation, but have certain common and robust characteristics. It appears that older adults may rely even more on bilateral arm reactions than do younger adults due to age-related deterioration in other postural control mechanisms. Although bilateral measures can also be relied on as a precursor for fall events, unilateral measurement may be adequate to detect actual falls.

The FM communicator 115 (e.g., shown in FIG. 3) may be small, light-weight, convenient and comfortable to wear during both wakefulness and sleep. The latter may be particularly important since many falls occur when elderly individuals (user 110) get up during the night to use the bathroom. The FMC module 320 may be sized at, for example, approximately 2.0 cm×1.2 cm×1.0 cm and weigh about 8 g. It appears that the wrists may be, by far, the most desirable locations for wearing the FM communicator(s) 115 in terms of ergonomics.

The FM system 100 (shown in FIG. 1) may be brought to market with multiple pricing options, ranging from outright purchase (e.g., for long-term use) to short-term lease (e.g., for use by an elderly person during the first few months of recuperation after a hospital stay). Independent of the option selected, the FM system 100 may be provided with, or without a monthly monitoring fee, since the user 110 may provide his/her own prioritized call list that may be stored in the transceiver 120 and/or the FM communicator 115. For those living independently, highest priority may likely be family members and friends; for residents of an elder care facility, first priority may be the facility security station. The availability of a fall/personal alert monitor without a required ongoing monthly fee may make the FM system 115 attractive and affordable to a wide segment of elderly individuals and their families. Payment plans may also be made available to users 110 who prefer paying a small monthly fee over time.

The invention has broader applications than monitoring a fall condition of the user 110, including, for example, sensing revolutions of wind turbine blades, or the like.

While the invention has been described in terms of exemplary embodiments, those skilled in the art will recognize that the invention can be practiced with modifications in the spirit and scope of the appended claims. These examples given above are merely illustrative and are not meant to be an exhaustive list of all possible designs, embodiments, applications or modifications of the invention.

What is claimed:

1. A communicator for autonomous monitoring, detecting and tracking of movement and orientation of a body or portion of a body, comprising:
   a device configured to monitor at least one of translational and rotational movement of the body;
   an altimeter configured to measure changes in height, wherein the altimeter comprises a high sensitivity pressure sensor; and
   a processor configured to specifically determine if an individual has experienced a hard fall event, has experienced a soft fall event, is exhibiting a susceptibility to a fall, or has experienced a near fall event based at least one of the monitored translational movement of the body, monitored rotational movement of the body, and measured changes in height of the body,
   wherein an alert condition is determined based on the translational and rotational movement of the body and changes in height of the body or portion of the body;
   wherein the altimeter comprises a temperature-compensated, calibrated pressure sensor having a clamped output.

2. The communicator according to claim 1, wherein the alert condition comprises:
   a hard fall event;
   a soft fall event;
   a susceptibility to a fall; or
   a near fall event.

3. The communicator according to claim 1, further comprising:
   a sensor configured to monitor biological functions of the body.

4. The communicator according to claim 1, further comprising:
   a storage configured to collect and store data for synchronous communication to a transceiver, wherein the data comprises any one or more of a date data, a time data, a location data, a biometric data and an alert condition data.

5. The communicator according to claim 1, wherein the device configured to monitor the translational and rotational movement of the body, or portion of a body, comprises one or more triaxial accelerometers.

6. The communicator according to claim 1, further comprising:
   one or more actuators configured to be actuated by a user to enable or disable an alert call,
   wherein the one or more actuators are configured to attach to the body.

7. The communicator according to claim 4, further comprising:
   a transceiver unit configured to convey the data stored in the storage to a transceiver,
   wherein the transceiver is configured to provide notification of alert events to one or more recipients.

8. A system that includes the communicator according to claim 7, wherein the system further includes the transceiver, the transceiver comprising:
   a communications device configured to record, log and track the data conveyed from the transceiver unit.

9. The system according to claim 8, wherein the transceiver comprises a storage that stores the recipient information.

10. The communicator according to claim 1, wherein the monitored translational and rotational movement of the body, include standing, walking, running, sitting, falling and lying down.

11. The communicator according to claim 7, wherein the transceiver unit is further configured to synchronize data with another communicator prior to monitoring translational and rotational movement of the body and measuring changes in height of the body or portion of the body.

12. A transceiver for autonomous monitoring, detecting and tracking of orientation, translational or rotational movement of a body, comprising:
   a transceiver unit configured to receive alert status data from a communicator that includes a processor configured to specifically determine if an individual has experienced a hard fall event, has experienced a soft fall event, is exhibiting a susceptibility to a fall, or has experienced a near fall event based at least one of the monitored translational movement of the body, monitored rotational movement of the body, and measured changes in height of the body using an altimeter configured to measure changes in height, wherein the altimeter comprises a high sensitivity pressure sensor; and
   a storage configured to hold recipient information associated with the communicator,
   wherein the transceiver unit is further configured to notify one or more recipients on the basis of the alert status data;
   wherein the altimeter comprises a temperature-compensated, calibrated pressure sensor having a clamped output.

13. The transceiver according to claim 12, wherein the transceiver unit is further configured to provide notification of an alert event to the recipient.

14. The transceiver according to claim 12, wherein the transceiver further comprises a communication device that is configured to record, log and track the alert status data.

15. A method for autonomously monitoring, detecting and tracking movements of a body, comprising:
   monitoring a translational and a rotational movement of the body or portion of the body;
   measuring a change in height of the body or a portion of the body using an altimeter configured to measure changes in height, wherein the altimeter comprises a high sensitivity pressure sensor;
   determining if an individual has experienced a hard fall event, has experienced a soft fall event, is exhibiting a susceptibility to a fall, or has experienced a near fall event based at least one of the monitored translational movement of the body, monitored rotational movement of the body, and measured changes in height of the body; and
   determining an alert event based on the translational and rotational movement of the body and the change in height of the body or portion of it;
   wherein the measuring a change in height of the body or a portion of the body using an altimeter comprises an altimeter comprising a temperature-compensated, calibrated pressure sensor having a clamped output.

16. The method according to claim 15, further comprising:
   generating an alert status data based on the determined alert event; and
   contacting one or more recipients based on the fall status data.

17. The method according to claim 16, further comprising:
   selecting a recipient from the contact list;
   retrieving a message to be conveyed to the recipient; and
   conveying the message to the recipient.

18. The method according to claim 17, further comprising:
   determining whether the recipient responds to the message.

19. The method according to claim 16, wherein the fall status data comprises:
   translational movement data;
   rotational movement data;
   height data;
   height change data;
   time data;
   date data;
   location data; or
   biometrics data.

20. The method according to claim 18, further comprising:
   activating a communication device to establish a communication session with the recipient, when the recipient responds to the message.

* * * * *